United States Patent [19]

Gambell et al.

[11] 4,272,451

[45] Jun. 9, 1981

[54] ACETONITRILE PROCESS WITH IMPROVED CATALYSTS

[75] Inventors: James W. Gambell; Steven R. Auvil, both of St. Louis, Mo.

[73] Assignee: Monsanto Company, St. Louis, Mo.

[21] Appl. No.: 106,776

[22] Filed: Dec. 26, 1979

[51] Int. Cl.³ .................... C07C 121/18; C07C 120/00
[52] U.S. Cl. .................................. 260/465.1; 423/376
[58] Field of Search ....................................... 260/465.1

[56] References Cited

U.S. PATENT DOCUMENTS 4,179,462  12/1979  Olivé et al. .................... 260/465.1

Primary Examiner—Joseph Paul Brust
Attorney, Agent, or Firm—Joseph D. Kennedy; James W. Williams, Jr.

[57] ABSTRACT

In the process for preparing acetonitrile from CO, $NH_3$ and $H_2$, molybdenum catalysts containing manganese or alkaline earths, and optionally alkali metals, are employed to improve selectivity to acetonitrile.

17 Claims, No Drawings

ACETONITRILE PROCESS WITH IMPROVED CATALYSTS

The present invention is concerned with a process for preparing acetonitrile. In particular, it involves a process in which modified molybdenum catalysts are employed, the catalyst containing a component such as a manganese or strontium compound along with molybdenum.

BACKGROUND OF THE INVENTION

A commonly assigned patent of G. and S. Olivé, U.S. Pat. No. 4,179,462 issued Dec. 18, 1979, describes a process in which acetonitrile is prepared by high temperature reaction of carbon monoxide, hydrogen and ammonia over a transition metal, with molybdenum metal in a reduced valence state being one of the prominent catalysts employed. The process is described as operable under various temperature and pressure conditions.

As discussed in the aforesaid application, acetonitrile is a known compound of recognized industrial value, and various approaches have been used in preparing it by reactions involving hydrocarbons, amines, acetic acid, etc. The aforesaid application provides a new route utilizing such relatively inexpensive and available raw materials as hydrogen, carbon monoxide and ammonia.

SUMMARY OF THE INVENTION

The present invention involves the use of a modified molybdenum catalyst in preparation of acetonitrile. It has been found that presence of manganese, strontium, barium or calcium components, along with molybdenum, permits a greater control over the reaction in directing it to desired acetonitrile product. In addition, small amounts of alkali metals, such as potassium and sodium, are further useful in improving selectivity of the reaction toward acetonitrile. Particularly useful catalysts utilize the modifiers with fairly substantial amounts of molybdenum oxides on catalyst supports.

DETAILED DESCRIPTION OF THE INVENTION

In the use of molybdenum catalyst in the contemplated production of acetonitrile, the molybdenum in the form of a soluble salt is usually impregnated on a catalyst support, and the dried catalyst precursor is then subjected to oxidizing conditions, followed by reducing conditions. This does not reduce the molybdenum completely to the metal but apparently leaves it on the average, in an oxidation state less than its maximum. Other components, such as manganese appear in some cases to affect the oxidation state and to retard the reduction of molybdenum below $MoO_2$.

The molybdenum with modifying metals may be used in unsupported form, or alternatively employ a support selected from activated alumina, silica gel, diatomaceous earth, thoria, ceria, silica alumina, and pumice, or generally any of the common refractory catalyst supports. From a practical standpoint there may be advantage in use of supports with respect to long term stability and retention of activity. The amounts of each metal additive will depend on the presence or absence of supports. Unsupported preparations may be used in stoichiometric ratios, $MnMoO_4$, $MgMoO_4$, or $SrMoO_4$ written in oxidized form. With supported catalysts the appropriate amount of each additive will depend on the nature of the support. With supports which do not interact strongly with molybdenum, such as silica gel, loadings of molybdenum on the order of 10% (by weight as molybdenum metal) are very effective. On the other hand, with supports which interact more strongly with molybdenum such as activated alumina, higher molybdenum loadings will be required; for example, loadings of molybdenum as high as 20% or even higher may be advisable for best results. It is understood that the molybdenum loading employed will depend, in part, on the surface area of the support, with higher surface areas calling for higher loadings. Illustrative loadings specified for silica gel and for activated alumina are appropriate for support materials with surface areas on the order of 300 and 200 $m^2g$ respectively (measured by Brunauer-Emmet-Teller method). While broad ranges of molybdenum can be employed, e.g. from 1% or preferably from 5% up to 20-30% or more by weight, there is advantage in selecting loadings for particular supports as indicated. Likewise, the preferred amount of alkaline earth and/or manganese to employ with molybdenum will depend on the support chosen. With weakly interacting supports the ratio (molar) of additive to molybdenum can be about 1:1 and give good results. With strongly interacting supports, the ratio will generally depend on molybdenum loadings; the lower the molybdenum loading the higher the ratio required. Thus, while 1:1 ratios may give good results at higher molybdenum loadings (on the order of 20% Mo calculated as $MoO_3$) at lower loadings more alkaline earth and/or manganese will be required for optimum catalyst performance. Thus, with activated alumina supports and molybdenum loadings of 10%, w/w, ratios of 1.5:1 or higher may be desirable. While particular ratios may be most useful, the molar ratio of modifying metal additive to molybdenum can vary widely, for example from about 0.1:1 to about 10:1, although generally there is no reason to use an amount of modifer over that which gives additional effect. Molar ratios of modifier to molybdenum will often be in the range of about 0.25:1 to about 4:1. Much of the description herein of the amounts and effects of modifying metals is particularly applicable to and based upon manganese modified molybdenum catalyst, but is considered generally applicable to other modified catalysts of the invention.

With alumina support, the alumina may interact with the molybdenum to some extent and thereby lessen the effect of the modifier component. When sufficient molybdenum is present for a monolayer on the support, there will be molybdenum which is free of strong interaction with the alumina. With lesser amounts of molybdenum, some will still be available for interaction or influence by the manganese or other modifier and the modifiers have effect. Moreover, the amount of molybdenum for a monolayer will vary with the surface area of the support, for example about 15.5 weight percent molybdenum, as metal, being sufficient for a support with surface area of 150 square meters per gram. In general it will be desirable to have both the molybdenum and modifying metal present in amounts so as to give an augmented effect from their joint presence on attainable selectivity to acetonitrile, and such amount can be referred to as effective combined amounts.

The catalysts utilized herein can be prepared by a variety of means, for example in accord with manufacture and treatment procedures described in the aforesaid U.S. Pat. No. 4,179,462. For example, water soluble salts of selected additives, e.g. molybdenum and manganese, or molybdenum and strontium, and optionally potassium, may be impregnated on a catalyst support and subjected to oxidizing conditions followed by reducing conditions.

Water soluble salts or complexes can be used in preparing the catalysts used in the present invention. For example, ammonium para molybdate and nitrates of alkaline earths, manganese and potassium have been employed. Other salts, or other methods of preparation will generally suffice to produce active catalysts for the present invention. Removal of the majority of water after impregnation can be accomplished by drying at about 100° C. Depending on the particular catalyst preparation in question, an oxidation treatment to convert the impregnated salt to an oxidized form of the metal(s) in question can be employed advantageously. The oxidation can be performed conveniently in air. The temperature of oxidation will, of course, depend on the additives present and also the presence of particular supports. For example, temperatures high enough to cause sublimation of molybdenum are to be avoided. Also, temperatures high enough to cause adverse effects on support properties likewise should be avoided; for example, calcination temperatures will generally be low enough when activated alumina is employed as support to avoid conversion of support to alpha alumina.

Catalysts employed in the present invention are generally employed in reduced form. This does not necessarily imply reduction to the metal. Rather, the oxidized catalyst form can be activated by treatment with hydrogen at elevated temperature, such as 500° C., thereby obtaining intermediate average valence between that of metal and of fully oxidized catalyst.

The molybdenum in the catalyst may be subject to some cycling in valence state during the reaction to prepare nitriles, but at times appears to be in an intermediate valence state. An $MoO_3$ component may be reduced prior to or during the reaction to $MoO_2$ and possibly still further to have a mixture of molybdenum in the zero, $+II$, $+III$ and $+IV$ valences. When molybdenum is supported on silica, a manganese component appears to some extent to retard the rate of reduction of the molybdenum, but this effect is less evident on alumina supports. The particular mechanism by which the modifier is effective is uncertain, and several mechanisms may be occurring, and such may possibly include effects on the carrier.

Moreover, it is known that carriers can influence reduction properties of molybdenum trioxides, with molybdenum trioxide itself being more readily reducible than molybdenum trioxide on silica, which reduces considerably more readily than molybdenum trioxide on alumina. The formation of molybdates with the carrier, which is particularly evident with alumina, can affect reducibility. The reduction is a dynamic occurrence with the rate depending on conditions, and during use as catalyst there may be counter actions serving to re-oxidize the molybdenum to higher oxidation states. However, aside from what other influences may be operative, it appears that in the effective molybdenum valences, the presence of a somewhat higher valence state tends to improve the selectivity to acetonitrile, and that there may be advantage in limiting the amount of molybdenum with average oxidation state below $Mo^{4\pm}$. Even so, the modifiers have the effects described herein and their use is contemplated as within the invention aside from what effect they have on the molybdenum valence state.

While the catalysts employed herein may be viewed for simplicity as comprising the molybdenum as molybdenum oxides, it is to be understood that the oxygen may be present in the form of hydroxyl groups, or oxyaluminum groups bound to the molybdenum, when the support is alumina.

The use of a support permits more efficient use of the active components. It will be recognized that there will be some variation in the results with different supports. Aluminas, particularly high surface area aluminas, give good results and appear to be among the better supports.

The active catalysts are generally formed prior to use by activating supported metal oxides on a support, e.g., $MoO_3$ and a modifying metal, under reducing conditions at elevated temperature, e.g. hydrogen atmosphere at 500° C. However, as the conditions for production of acetonitrile are reducing, involving hydrogen, carbon monoxide and ammonia, the catalyst materials can be activated in situ by being subjected to appropriate reaction conditions in the presence of reactants.

The addition of small but effective amounts of alkali metal to the modified molybdenum catalysts provides a slight additional increase in selectivity to acetonitrile. The amounts of alkali metal will vary with the particular alkali metal, manganese or alkaline earth component, and support, but will usually be in the range of about 0.1 to about 2% by weight of the catalyst calculated as alkali metal, and often will be less than 1% by weight, e.g. about 0.1% to 0.75% by weight, and potassium is the preferred metal for use in the indicated ranges, although sodium and other alkali metals can be employed. The small amounts which are effective in improving selectivity can be readily determined for particular catalysts.

The manganese, strontium or other alkaline earths appears to be present in some positive valence state as oxides, molybdates or the like, but may be subject to oxidation-reduction during use, and in any event such components are found to be effective when used as taught herein aside from what specific compounds may be involved. Similarly, the alkali metals may be present as oxides or other compounds and have the desired effect.

When molybdenum is dispersed on a refractory support, the present invention includes use of such catalyst containing manganese or alkaline earth metal components alone or in admixture, as additional component, e.g. manganese, strontium, calcium, barium, magnesium, beryllium, and particularly includes such catalysts in which the support is alumina. The stated components can generally be used in the ranges of amounts set forth herein and in the form resulting from the types of catalyst preparations and uses described herein.

The catalysts described herein will include the named active components and also generally a catalyst support or carrier. Such components are sufficient for the desired effectiveness of the catalysts. Other components can also be present, although not generally necessary. Other metal components if present will have varied effect. Many will have little significant effect, while a few will have some slight benefit. Some will tend to catalyze different or side reactions with detriment to acetonitrile selectivity. Molybdenum with the other described components may still have an augmented effect, even if impaired to some extent by presence of additional components. However it will generally be preferred that the catalysts consist essentially of designated components on a support, with "consisting essentially" having its usual meaning of excluding presence of other components in amounts which would alter the basic character of the compositions.

The acetonitrile forming reaction is suitably carried out by conducting the reactants over the catalyst at elevated temperature with a residence time sufficient to effect the reaction. The reaction can conveniently be demonstrated utilizing a glass (high temperature) reactor tube with capacity for about 20 cm$^3$ of catalyst packed into the tube and held with quartz wool plugs. As a normal charge, about 10 cm$^3$ (bed depth about 5 cm) catalyst is employed. A glass thermowell extends along the central axis of the reactor tube, through the catalyst bed, permitting temperature measurement by suitably positioning a thermocouple. The tube is contained within a metal shell to permit safe operation at elevated pressure, and placed within a radiantly heated furnace, and provided with temperature controls and means for pre-heating the feed gas. The components of the feed gas are mixed prior to entering the reactor, and on-line gas chromatographs are available for measuring feed and product streams. The described apparatus is suitable for use at moderately elevated pressures. Modifications can be made for operations at higher pressures, or types of equipment generally employed for high pressure operations can be used. In general it is desirable to employ glass or other refractory materials as components or liner materials in reactant zones to avoid possible effects of metal contact upon the reactant gases. The reactor as described can be used but with a steel container with a glass liner for the reaction zone. A gold coating on the steel has been found effective in limiting possible effects of contact of the gases with the metal.

EXAMPLES 1 to 17

Employing the procedure described above, the effect of manganese on molybdenum catalyzed production of acetonitrile is demonstrated under the conditions described below and set forth in Table 1. The procedures employed a reaction temperature of 500° C. and pressure of 100 psi gauge. In the Table HCN, ACN and PN refer respectively to hydrogen cyanide, acetonitrile and propionitrile.

TABLE 1

The Effect of Manganese and Potassium Promotion of Molybdenum Containing Catalysts

| Example | Catalyst[1] (wt.-%) | GHSV (@STP) | Reactant Gases | | | % Conversion CO | Molar Selectivity to Reactions | | | | | | | |
|---|---|---|---|---|---|---|---|---|---|---|---|---|---|---|
| | | | CO | NH$_3$ | H$_2$ | | Disp* | Shift | CH$_4$ | C$_2$'s | C$_3$'s | HCN | ACN | PN |
| Alumina Supported Prep's[2] | | | | | | | | | | | | | | |
| 1. | 20% Mo | 1250 | 1 | 2.0 | 0.5 | 42.6 | 5.2 | 44.0 | 5.8 | 1.4 | 0.1 | 6.8 | 34.0 | 2.7 |
| 2. | 9.2% Mn-16% Mo | 1300 | 1 | 2.0 | 0.5 | 47.6 | 5.4 | 43.9 | 5.1 | 1.3 | — | 5.4 | 36.4 | 2.5 |
| 3. | 6.9% Mn-18% Mo | 1350 | 1 | 2.0 | 0.5 | 45.7 | 3.0 | 43.4 | 5.6 | 1.1 | — | 4.4 | 39.5 | 3.1 |
| 4. | 11% Mo | 1370 | 1 | 2.1 | 0.49 | 41.3 | 6.8 | 43.1 | 7.3 | 1.5 | 0.1 | 6.3 | 32.4 | 2.5 |
| 5. | 6.6% Mn-8.7% Mo | 1330 | 1 | 2.0 | 0.50 | 38.1 | 6.4 | 42.9 | 4.7 | — | — | 6.4 | 36.9 | 2.7 |
| 6. | 5.1% Mn-8.9% Mo | 1340 | 1 | 2.0 | 0.50 | 39.0 | 5.3 | 43.8 | 5.5 | — | — | 6.3 | 36.2 | 2.8 |
| 7. | 3.5% Mn-9.1% Mo | 1360 | 1 | 2.0 | 0.50 | 37.0 | 6.2 | 43.4 | 4.3 | — | — | 8.1 | 35.5 | 2.6 |
| 8. | 5.1% Mn-8.9% Mo | 1280 | 1 | 2.1 | 0.48 | 38.9 | 8.3 | 42.2 | 4.7 | — | — | 6.6 | 35.6 | 2.6 |
| 9. | 5.1% Mn-8.9% Mo 0.75% K | 1345 | 1 | 2 | 0.49 | 40.6 | 5.5 | 42.00 | 3.7 | — | — | 9.2 | 37.7 | 2.9 |
| Silica gel Supported Prep's[3] | | | | | | | | | | | | | | |
| 10. | 10% Mo | 810 | 1 | 1 | 1 | 47.6 | 4.1 | 43.8 | 16.8 | 7.9 | 3.5 | 1.0 | 20.2 | 2.7 |
| 11. | 5.7% Mn-10% Mo | 270 | 1 | 1.5 | 1 | 46.5 | 2.4 | 44.0 | 10.4 | 4.3 | 1.6 | 1.3 | 31.9 | 4.2 |
| 12. | 5.7% Mn-10% Mo | 570 | 1 | 1 | 1 | 39.2 | 4.7 | 42.8 | 11.8 | 5.5 | 2.6 | 1.4 | 26.9 | 4.4 |
| 13. | 8.4% Mn-8.5% Mo | 1000 | 1 | 1 | 1 | 33.2 | — | 45.2 | 7.4 | 3.6 | 1.1 | 3.9 | 33.2 | 5.5 |
| 14. | 8.4% Mn-8.5% Mo | 1000 | 1 | 1 | 1 | 23.7 | 1.3 | 43.5 | 6.1 | 0.2 | — | 9.2 | 35.9 | 3.9 |
| 15. | 8.4% Mn-8.5% Mo | 1000 | 1 | 1 | 1 | 21.3 | 4.7 | 42.0 | 4.7 | — | — | 13.6 | 32.5 | 2.4 |
| 16. | 8.4% Mn-8.5% Mo 2.0% K | 1000 | 1 | 1 | 1 | 19.7 | 9.4 | 39.7 | 3.5 | — | — | 16.2 | 29.5 | 1.7 |
| 17. | MnMoO$_4$(neat) | 620 | 1. | 1.2 | 0.41 | 50.9 | 13.7 | 42.0 | 2.9 | 0.6 | — | 1.4 | 34.5 | 4.9 |

*this reaction is assumed to be $CO + 2MoO_2 = Mo_2C + 5CO_2$
[1]weight percentages expressed as percentages based on element in oxidized catalyst assuming MoO$_3$, MnO and K$_2$O as components present.
[2]alumina employed was a 5 × 8 mesh spherical crystalline type of alumina; low soda (about 0.05 wt.-%),surface area about 180 m$^2$/g, macropore volume (d greater than 700 angstroms about 0.2 cc/g); Lot BR-2025 from Kaiser Chemical Company.
[3]silica gel employed was commercially available Grade 59 silica gel from Davison Chemical, a division of W.R. Grace.

The improvement in acetonitrile selectivity is evident from comparison of Example 1 to Examples 2 (1:1 mole ratio of Mn:Mo) and 3 (2:3 mole ratio of Mn:Mo), both the selectivity and conversion being higher with the manganese containing catalyst, and the conversion actually increasing with increasing manganese content. The benefit of the manganese addition employing alumina supports was also obtained when the molybdenum loading was lower, as seen by comparing Examples 5–7 to Example 4.

The addition of alkali or alkaline earths to manganese-molybdenum catalysts is also beneficial and can result in a further increase in acetonitrile selectivity, as illustrated by comparing Example 9 to Example 8, and Examples 13 to 16 for a silica supported catalyst. Quadratic interpolation from the latter examples predicts an optimum 2.6 percentage increase in selectivity over the potassium free case at a 0.47 weight percent potassium loading. It is expected that the optimum amounts of each component will vary with the amounts of the other two components present, and also with the support.

The present process can be carried out in general in accordance with the conditions described in the aforesaid Olivé patent. The molar ratio of carbon monoxide, hydrogen and ammonia is generally in the range of from about 1:0.1–10:0.05–4. A temperature high enough to effect the desired reaction will be employed, and with the present molybdenum catalysts this will usually be at least 350° C. and preferably in excess of 450° C. up to 550° C. or 600° C. Sub-atmospheric, ambient, or super-atmospheric pressures can be employed. Elevated pressures, at least in moderate ranges up to 1000 psi gauge, may give product distributions similar to those at lower pressures unless special factors are involved. While thermodynamic considerations indicate that amine forming reactions are favored by elevated pressure, this was not found to be a significant problem with the molybdenum catalysts at the temperatures employed. The elevated pressures permit higher volumetric productivity, but, of course, require more expensive equipment. The reaction is operative over a broad range of reaction times or space velocities, e.g. gaseous hourly space velocities from about 50 to 15,000 or more. The space velocity is the ratio of the volume of gases (at standard temperature and pressure) charged per hour to volume of reaction space. However, the desired reaction is equilibrium limited, so that it is generally desirable to employ a relatively high space velocity as there is generally no reason for trying to continue the reaction post equilibrium. The optimum space velocity for maximum practical conversion with efficient reactor usage will vary with temperature and pressure, but will generally be in the range of about 200 to 2,000 reciprocal hours. Under usual conditions, the selectivity to acetonitrile declines rapidly above CO conversions of 40 to 50% or so, where selectivity to acetonitrile may be around 40%. However, it has been found that selectivity to acetonitrile can be improved by adding substantial amounts of carbon dioxide to the feed stream, and accepting much lower conversions, as described in co-pending application Ser. No. 106,775 filed Dec. 26, 1979 of Steven R. Auvil and Charles R. Penquite. For example, data indicate that with a particular catalyst an acetonitrile selectivity of 50% is obtainable (at 500° C. and 100 psi gauge) by utilizing a $CO_2/CO$ ratio of 0.68 and running to conversion of 16%. For a 60% selectivity, the corresponding conversion is 7-8%. These values will vary with the particular catalyst and modifier as well as with other factors such as temperature and pressure, as further illustrated by examples herein. The choice of conditions for operation in practical terms will depend upon reactor characteristics and desired through-put and efficiency balanced with consideration of product yield. When carbon dioxide is used, there is advantage to operating at elevated pressure, such as pressure over 300 or 500 psi gauge up to 1000 psi gauge or more, and employing carbon dioxide at ratios of at least 1.5-2 or more moles $CO_2$ to mole CO, as disclosed in the aforesaid copending application Ser. No. 106,775, which concerns the use of carbon dioxide in the process to improve selectivity to acetonitrile. Any of the procedures in the co-pending application can be used in the present process, and there appears to be definite advantage in the use of carbon dioxide in the process.

The advantages of various catalysts will vary with conditions. Manganese used with molybdenum appears to provide improvement in selectivity to acetonitrile over a fairly broad range of conditions. Strontium is particularly effective at elevated pressures where it causes a significant improvement in selectivity. The improved selectivity with strontium may be particularly important in processes utilizing high pressure with carbon dioxide addition and trying to achieve high selectivity while retaining acceptable conversions. In general it will be desirable to use the modified catalysts under conditions resulting in the desired augmented effect of the catalyst components.

EXAMPLE 18

Employing general procedures utilized for Examples 1 to 17, the production of acetonitrile with various modified molybdenum catalysts was carried out under the conditions and with the results set forth in Table 2. The supported catalysts utilized were prepared in accord with the procedure in Example 21, impregnating the support with molybdenum, and then with the nitrate salt of calcium, mangnesium, manganese or strontium in the manner in which strontium nitrate was added in Example 21. The unsupported catalysts were prepared in accord with the procedure described in Example 20 for magnesium molybdate, but starting with calcium molybdate or barium molybdate powders obtained from Climax Molybdenum Company.

It is apparent that in general the use of the metal modifiers greatly improved selectivity to acetonitrile over that obtained with the unmodified molybdenum. It is also shown that a decrease in space velocity with a calcium molybdate catalyst, increases selectivity to acetonitrile and higher nitriles. The barium molybdate surface area was undoubtedly low, resulting in low CO conversion, high selectivity to HCN and low selectivity to acetonitrile. The selectivity to nitriles (HCN+ACN) is high, 52%. Placing the Ba $MoO_4$ on a high surface area support and/or running the reaction at much lower space velocities should increase the CO conversion and increase the selectivity to acetonitrile relative to HCN, producing the good performance expected of a barium modified molybdenum catalyst from the relationship of barium to other modifiers used with advantage herein.

TABLE 2

IMPROVED SELECTIVITIES TO ACETONITRILE WITH ALKALINE EARTH ADDITION TO SUPPORTED AND UNSUPPORTED MOLYBDENUM CATALYSTS

Temperature = 500° C., Pressure = 500 psig, GHSV = 5000 @ STP
$CO:NH_3:H_2$ = 1:2.0:.53 (mol ratio)

| Catalyst | CO Conversion % | Selectivities (%) | | | | |
|---|---|---|---|---|---|---|
| | | $CO_2$ | HCN | ACN | Higher Nitriles | Hydrocarbons |
| 20.5 parts Mo-100 parts alumina | 55 | 49.0 | 3.9 | 27.5 | 4.2 | 15.4 |
| 8.6 parts Ca-20.5 parts Mo 100 parts alumina | 45 | 47.0 | 11.6 | 34.8 | 3.4 | 3.2 |
| 14.4 parts $M_n$-20.5 parts Mo 100 parts alumina | 48 | 47.1 | 4.6 | 35.8 | 3.6 | 9.0 |
| 5.2 parts Mg-20.5 parts Mo 100 parts alumina | 50 | 47.5 | 3.8 | 37.2 | 3.9 | 7.6 |
| 11.6 parts Sr-20.5 parts Mo 100 parts alumina | 42 | 46.9 | 8.5 | 35.2 | 1.4 | 8.1 |
| Calcium molybdate GHSV 5,000 | 26 | 47.8 | 14.2 | 33 | 1.9 | 3.1 |
| (Unsupported) GHSV 2,500 | 35 | 47.5 | 8.0 | 37.2 | 3.0 | 4.3 |

TABLE 2-continued
IMPROVED SELECTIVITIES TO ACETONITRILE WITH ALKALINE EARTH ADDITION TO SUPPORTED AND UNSUPPORTED MOLYBDENUM CATALYSTS Temperature = 500° C., Pressure = 500 psig, GHSV = 5000 @ STP
CO:NH$_3$:H$_2$ = 1:2.0:.53 (mol ratio)

| Catalyst | CO Conversion % | Selectivities (%) | | | | |
|---|---|---|---|---|---|---|
| | | CO$_2$ | HCN | ACN | Higher Nitriles | Hydrocarbons |
| Barium molybdate GHSV = 5,000 (Unsupported) | 9 | 43.0 | 45.0 | 7.0 | — | 5 |

EXAMPLE 19

Employing a reactor tube as described herein, carbon monoxide, ammonia and hydrogen were conducted over a modified molybdenum catalyst at temperature of 500° C. and pressure of 100 psi gauge to produce acetonitrile. The reactants in the feed stream were employed in ratios on a molecular basis, CO:NH$_3$:H$_2$ of 1:1.92:0.37. Varying amounts of carbon dioxide were added to the feed, as reported below in Table 3.

TABLE 3

| Run | CO$_2$/CO Mole ratio | GHSV (STP) | % CO Conversion | Selectivity to ACN |
|---|---|---|---|---|
| 1 | 0 | 1305 | 48 | 39.7 |
| 2 | .22 | 1390 | 37.5 | 41.6 |
| 3 | .36 | 1445 | 29.5 | 42.4 |
| 4 | .57 | 1530 | 21.5 | 46.8 |
| 5 | .7 | 1580 | 15.5 | 49.3 |
| 6 | .88 | 1655 | 12.5 | 51.2 |

The catalyst utilized was a molybdenum on alumina catalyst which also contained manganese, with 8.9% molybdenum and 5.1% manganese, the percentage being by weight.

It can be seen from the results above that selectivity to acetonitrile is improved and increases with increasing amounts of carbon dioxide. However the conversion declines as the amount of carbon dioxide increases.

The catalyst utilized in Example 19 was prepared as follows. A 5×8 mesh gel derived alumina support (Kaiser B$_R$-2025) with low Na$_2$O content was calcined 5 hours at 600° C. in air. Utilizing minimum solution technique, a 20 gram amount of the support was impregnated with ammonium paramolybdate ((NH$_4$)$_6$ Mo$_7$O$_{24}$·4H$_2$O, powder), 4.09 grams, dissolved in 14.1 ml water (10% excess water). The material was then air dried at 120° C. for 3 hours and calcined for 3 hours at 600° C. The calcined material was then impregnated with 14.1 ml aqueous solution containing 8.28 grams of Mn(NO$_3$)$_2$ (diluted with water from 50% by weight aqueous solution). The material was then air dried at 120° C. for 3 hours and calcined for 3 hours at 600° C. The impregnation with Mn(NO$_3$)$_2$, drying and calcination was then repeated. (The double impregnation was used because of the dilute Mn(NO$_3$)$_2$ used). The catalyst was used directly in the above acetonitrile preparation. The catalyst had 8.9 weight percent Mo and 5.1 weight percent Mn on alumina, surface area of 148 m$^2$/gm. A uniform pretreatment of the catalyst in the reactor was employed, involving heating to 200° C. under nitrogen, gradually heating to 500° C. under 44% hydrogen in nitrogen, and then holding about 12 hours under hydrogen.

EXAMPLE 20

Using a reactor of the type described herein, adapted for use at pressure up to 1000 psi gauge, it was found that increased pressures improved the conversions obtainable in the presence of relatively high amounts of carbon dioxide. The data presented in Table 3 were obtained employing an unsupported magnesium molybdate catalyst operating at 500 psi (gauge) and 500° C. The CO$_2$:CO molar feed ratio was varied from run to run while the CO:NH$_3$:H$_2$ molar feed ratio was held constant at 1:2.94:0.27 in all runs. In order to keep the reactor running as near to equilibrium as possible the gas hourly space velocity (STP) was reduced as increased amounts of CO$_2$ were added to the feed. Unsupported molybdenum trioxide under these same conditions-without CO$_2$ present-gives CO conversion 55%

| Selectivites | |
|---|---|
| ACN | 28.5 |
| HCN | 8.6 |
| CO$_2$ | 46.5 |
| Hydrocarbons | 13.0 |
| Higher nitriles | 3.4 |

This allows a comparison to be made between the unsupported MgMoO$_4$ and unsupported MoO$_3$.

The results in Table 4 show clearly the beneficial influence of CO$_2$ addition to the feed gases. Without CO$_2$ addition, Run No. 1, only 37.9% of the CO converted results in acetonitrile formation with 45.8% of the CO converted lost to CO$_2$. However, adding 2.74 moles of CO$_2$ per mole of CO in the feed, Run No. 5, increases the CO selectivity to acetonitrile to 79.7% with essentially no CO loss to CO$_2$.

TABLE 4
Improved Carbon Monoxide Selectivities To Acetonitrile With Various Amounts of Carbon Dioxide Added To The Feed.

Catalyst: Unsupported Magnesium Molybdate
Temperature: 500° C.
Pressure: 500 psi (gauge)
CO:NH$_3$:H$_2$ molar feed ratio: 1:2.94:0.27

| Run No. | CO$_2$/CO mole ratio | GHSV @ STP | % CO Converted | % Selectivity* | | |
|---|---|---|---|---|---|---|
| | | | | Acetonitrile | HCN | CO$_2$ |
| 1 | 0 | 8040 | 61.8 | 37.9 | 3.0 | 45.8 |
| 2 | 1.96 | 3970 | 17.0 | 58.4 | 11.8 | 23.3 |
| 3 | 2.21 | 4000 | 14.7 | 59.9 | 14.1 | 18.0 |
| 4 | 2.50 | 2500 | 17.0 | 66.7 | 8.3 | 16.0 |
| 5 | 2.74 | 2600 | 13.7 | 79.7 | 11.5 | 0 |

*Remaining selectivities are to methane and propionitrile - small amounts of C$_2$ and C$_3$ hydrocarbons were also observed in Run #1.

The magnesium molybdate catalyst utilized above was prepared by tableting magnesium molybdate powder, without binding agents or lubricants, directly in a pellet press. The resulting pellets were right cylinders, nominally ⅛ inch diameter and ⅛ inch length. The pellets were broken into 10×20 mesh particles for use, and used directly, being activated to the extent needed by conditions in the reactor. The catalyst is designated as unsupported magnesium molybdate, $MgMoO_4$, with such reduction as occurs in use. Magnesium molybdate and molybdenum trioxide utilized for the catalyst was obtained from Climax Molybdenum Company, 1270 Avenue of the Americas, New York, N.Y. 10020. The $MgMoO_4$ can be prepared by reacting magnesium chloride, $MgCl_2$, with silver molybdate, $Ag_2MoO_4$, in aqueous solution in accord with a procedure described in "The System Magnesium Molybdate-Water and the 25° C. Isotherm of the System $MgMoO_4$-$MgCl_2$-$H_2O$," by John E. Ricci and William F. Linke, J.Am.Chem.Soc. 73, 3603, (1951).

EXAMPLE 21

Using a reactor of the type described herein, adapted for use at pressures up to 1000 psi gauge, it was found that increased pressure improved the conversions obtainable in the presence of relatively high amounts of carbon dioxide. From data obtained employing a molybdenum catalyst modified with strontium, the following is postulated as illustrative of good operating conditions and results. A reactor feed is employed with $CO:NH_3:H_2:CO_2$ in mole ratios of 1:2:0.5:2.3, at a space velocity (STP) of 500 reciprocal hours, and temperature of 500° C. at 815 psi (gauge). From this a 19% conversion of carbon monoxide is expected, with a selectivity to acetonitrile of 81% based on carbon monoxide. While of less interest to the present process, the selectivities based on ammonia and hydrogen are projected as 91% and 78% respectively. The strontium catalyst utilized for obtaining data was prepared as follows. As support 1/16 inch extruded alumina (Linde, type 60–503) with low iron content was utilized. The support was calcined 5 hours at 600° C. in air prior to use, and had 215 $m^2$/gram surface area. In order to obtain the desired molybdenum loading, successive impregnations were made involving impregnation of 25 grams of the support with 4.71 gram ammonium paramolybdate powder dissolved in 20.6 cc water, followed by air drying at 120° C. for 2 hours, and calcining for three hours at 500° C., and then repetition of the impregnation, drying and calcining steps. The molybdenum impregnated alumina was then impregnated with strontium nitrate, employing 5.56 grams strontium nitrate in 8 ml water for 12.72 grams of the molybdenum impregnated alumina. The material was then air dried at 120° C. for 2 hours and calcined in a muffle furnace for 5 hours at 600° C. The resulting material contained 13 weight percent Mo and 14.6 weight percent Sr (both metal basis) on alumina, and was used directly in reactions as described herein.

What is claimed is:

1. In a process of preparing acetonitrile by reaction of carbon monoxide, hydrogen and ammonia in molar ratio of approximately 1:0.1–10:0.5–4, at a temperature over about 450° C. over a molybdenum catalyst, the improvement which comprises utilizing catalyst consisting essentially of (a) unsupported molybdates of manganese, calcium, magnesium or strontium; or (b) a high surface area refractory support and molybdenum with additional additive which interacts therewith selected from compounds of manganese, strontium, magnesium and calcium, with such additive being present in molar ratio to molybdenum in the range of about 0.25:1 to about 4:1; and from zero up to about 2% of alkali-metal compound.

2. The process of claim 1 in which the catalyst contains an alkali metal component.

3. The process of claim 1 in which the catalyst contains a potassium component.

4. The process of claim 1 in which the reaction is conducted at a temperature over 450° C. and at a pressure in excess of 300 psi gauge.

5. The process of claim 1 in which the catalyst comprises a molybdenum component and a strontium component.

6. The process of claim 1 in which the catalyst comprises a molybdenum component and a manganese component.

7. The process of claim 5 in which the catalyst comprises a potassium component.

8. The process of claim 6 in which the catalyst comprises a potassium component.

9. The process of claim 1 in which the molybdenum is employed on a support in an amount of at least 3% by weight.

10. The process of claim 1 in which the catalyst contains manganese or strontium.

11. The process of claim 1 in which the molybdenum is mainly in positive valence states in the range from 2 to 4.

12. The process of claim 1 in which the catalyst preparation has involved reduction of the molybdenum to a lower average valence.

13. The process of claim 1 in which the molybdenum is present on a support in an amount of about 5% to about 20% by weight and has an average valence over 2 and the process is operated at a temperature in the range of about 450° to 600° C. and pressures from ambient up to 1000 psi gauge.

14. The process of claim 13 in which manganese is present in mole ratio to molybdenum of 0.25:1 to 4:1.

15. The process of claim 13 in which strontium is present in mole ratio to molybdenum of 0.25:1 to 4:1 and the process is operated at pressure over 300 psi gauge.

16. The process of claim 1 in which sodium or potassium is present in an effective amount less than 1% by weight.

17. The process of claim 1 in which an alumina support is employed.

* * * * *